(12) United States Patent

Blair et al.

(10) Patent No.: US 12,636,045 B2

(45) Date of Patent: *May 26, 2026

(54) RESORPTION-CONTROLLED COMPRESSION DEVICES AND PROCESSES FOR MAKING AND USING THE SAME

(71) Applicant: MedShape, Inc., Atlanta, GA (US)

(72) Inventors: Jeremy Webster Blair, Atlanta, GA (US); Ryan Walter O'Flaherty, Atlanta, GA (US); David Lee Safranski, Atlanta, GA (US)

(73) Assignee: MEDSHAPE, INC., Atlanta, GA (US)

( * ) Notice: Subject to any disclaimer, the term of this patent is extended or adjusted under 35 U.S.C. 154(b) by 180 days.

This patent is subject to a terminal disclaimer.

(21) Appl. No.: 18/680,788

(22) Filed: May 31, 2024

(65) Prior Publication Data

US 2024/0315735 A1     Sep. 26, 2024

Related U.S. Application Data

(63) Continuation of application No. 17/685,163, filed on Mar. 2, 2022, now Pat. No. 12,023,068.

(Continued)

(51) Int. Cl.
| | |
|---|---|
| *A61B 17/70* | (2006.01) |
| *A61B 17/86* | (2006.01) |

(Continued)

(52) U.S. Cl.
CPC .......... *A61B 17/702* (2013.01); *A61B 17/866* (2013.01); *A61L 31/128* (2013.01); *A61L 31/148* (2013.01); *A61B 2017/00004* (2013.01)

(58) Field of Classification Search
CPC ............................ A61B 17/702; A61B 17/866
See application file for complete search history.

(56) References Cited

U.S. PATENT DOCUMENTS

| 262,635 A | 8/1882 | Adams |
|---|---|---|
| 2,632,356 A | 3/1953 | Thiel |

(Continued)

FOREIGN PATENT DOCUMENTS

| CA | 19966 S | 6/1955 |
|---|---|---|
| CA | 50730 S | 1/1983 |

(Continued)

OTHER PUBLICATIONS

International Search Report and Written Opinion mailed May 13, 2022 for PCT/US2022/17414.

(Continued)

*Primary Examiner* — Christian A Sevilla

(74) *Attorney, Agent, or Firm* — Husch Blackwell LLP; Bryan D. Stewart

(57)     ABSTRACT

A medical device can include a first anchor for attachment to a first bone fragment and a second anchor for attachment to a second bone fragment. The second anchor attachment can be coupled to the first anchor via a compression element between the first anchor and the second anchor. The medical device can include a resorbable element maintaining the first anchor and the second anchor at a first distance. The resorbable element can be configured to at least partially resorb after insertion into a patient. After the resorbable element is at least partially sorbed, the compression element forces the first anchor and/or the second anchor to translate such that the first anchor and the second anchor are at a second distance, thereby compressing the first bone fragment and the second bone fragment.

17 Claims, 7 Drawing Sheets

Related U.S. Application Data

(60) Provisional application No. 63/155,322, filed on Mar. 2, 2021.

(51) Int. Cl.
| | |
|---|---|
| *A61L 31/12* | (2006.01) |
| *A61L 31/14* | (2006.01) |
| *A61B 17/00* | (2006.01) |

(56) References Cited

U.S. PATENT DOCUMENTS

| | | | |
|---|---|---|---|
| 2,867,807 | A | 1/1959 | Anstett |
| D193,140 | S | 7/1962 | Brown |
| 3,433,220 | A | 3/1969 | Zickel |
| 3,499,359 | A | 3/1970 | Yrjanainen |
| 3,611,708 | A | 10/1971 | Moore et al. |
| D227,976 | S | 7/1973 | Barth et al. |
| 3,969,975 | A | 7/1976 | Krol |
| 3,986,504 | A | 10/1976 | Avila |
| 4,175,555 | A | 11/1979 | Herbert |
| 4,269,180 | A | 5/1981 | Dall et al. |
| 4,402,445 | A | 9/1983 | Green |
| 4,452,236 | A | 6/1984 | Utsugi |
| 4,454,875 | A | 6/1984 | Pratt et al. |
| 4,537,185 | A | 8/1985 | Stednitz |
| D281,814 | S | 12/1985 | Pratt et al. |
| 4,570,623 | A | 2/1986 | Ellison et al. |
| D286,442 | S | 10/1986 | Korthoff et al. |
| 4,665,906 | A | 5/1987 | Jervis |
| 4,667,664 | A | 5/1987 | Taylor |
| 4,827,917 | A | 5/1989 | Brumfield |
| 4,865,025 | A | 9/1989 | Buzzi |
| 4,889,111 | A | 12/1989 | Azer |
| 4,913,137 | A | 4/1990 | Azer et al. |
| 4,983,176 | A | 1/1991 | Cushman et al. |
| 5,019,079 | A | 5/1991 | Ross |
| 5,034,013 | A | 7/1991 | Kyle |
| 5,057,103 | A | 10/1991 | Davis |
| 5,067,957 | A | 11/1991 | Jervis |
| 5,112,333 | A | 5/1992 | Fixel |
| 5,120,175 | A | 6/1992 | Arbegast et al. |
| 5,265,456 | A | 11/1993 | Kennedy et al. |
| 5,366,479 | A | 11/1994 | McGarry et al. |
| 5,415,660 | A | 5/1995 | Campbell |
| 5,454,814 | A | 10/1995 | Comte |
| 5,489,284 | A | 2/1996 | James |
| 5,505,733 | A | 4/1996 | Justin |
| 5,505,734 | A | 4/1996 | Caniggia |
| 5,620,445 | A | 4/1997 | Brosnahan |
| 5,632,746 | A | 5/1997 | Middleman et al. |
| D379,855 | S | 6/1997 | Perry |
| 5,653,709 | A | 8/1997 | Frigg |
| 5,658,287 | A | 8/1997 | Hofmann |
| 5,662,655 | A | 9/1997 | Laboureau et al. |
| 5,720,754 | A | 2/1998 | Middleman et al. |
| 5,766,174 | A | 6/1998 | Perry |
| 5,820,628 | A | 10/1998 | Middleman et al. |
| 5,836,066 | A | 11/1998 | Ingram |
| 5,855,579 | A | 1/1999 | James |
| 5,882,444 | A | 3/1999 | Flomenblit |
| 5,904,690 | A | 5/1999 | Middleman et al. |
| 5,928,235 | A | 7/1999 | Friedl |
| 5,964,768 | A | 10/1999 | Heubner |
| 5,964,770 | A | 10/1999 | Flomenblit et al. |
| 5,976,138 | A | 11/1999 | Baumgart |
| 6,001,101 | A | 12/1999 | Augagneur |
| 6,048,344 | A | 4/2000 | Schenk |
| 6,093,192 | A | 7/2000 | Abel |
| 6,123,708 | A | 9/2000 | Kilpela |
| 6,168,595 | B1 | 1/2001 | Durham |
| 6,187,009 | B1 | 2/2001 | Herzog et al. |
| 6,200,317 | B1 | 3/2001 | Aalsma |
| 6,224,600 | B1 | 5/2001 | Protogirou |
| 6,228,086 | B1 | 5/2001 | Wahl |
| 6,261,290 | B1 | 7/2001 | Friedl |
| 6,306,140 | B1 | 10/2001 | Siddiqui |
| 6,306,141 | B1 | 10/2001 | Jervis |
| 6,488,684 | B2 | 12/2002 | Bramlet |
| 6,533,805 | B1 | 3/2003 | Jervis |
| 6,579,293 | B1 | 6/2003 | Chandran |
| 6,637,995 | B1 | 10/2003 | White |
| 6,688,828 | B1 | 2/2004 | Post |
| 6,783,529 | B2 | 8/2004 | Hover |
| 6,786,908 | B2 | 9/2004 | Hover |
| 6,808,527 | B2 | 10/2004 | Lower |
| 6,921,400 | B2 | 7/2005 | Sohngen |
| 6,986,774 | B2 | 1/2006 | Middleman et al. |
| 7,005,018 | B2 | 2/2006 | Julien |
| 7,018,380 | B2 | 3/2006 | Cole |
| 7,056,322 | B2 | 6/2006 | Davison |
| 7,232,443 | B2 | 6/2007 | Zander |
| 7,455,673 | B2 | 11/2008 | Gotfried |
| D586,915 | S | 2/2009 | Grim |
| D604,846 | S | 11/2009 | Hintermann |
| 7,648,599 | B2 | 1/2010 | Berendt |
| D611,145 | S | 3/2010 | Khalil |
| D611,225 | S | 3/2010 | Khalil |
| 7,708,738 | B2 | 5/2010 | Fourcault |
| 7,722,610 | B2 | 5/2010 | Viola et al. |
| 7,731,738 | B2 | 6/2010 | Jackson |
| 7,763,022 | B2 | 7/2010 | Speitling |
| 7,771,428 | B2 | 8/2010 | Siravo |
| 7,794,483 | B2 | 9/2010 | Capanni |
| D625,417 | S | 10/2010 | Fox et al. |
| D625,591 | S | 10/2010 | MacDonald et al. |
| D625,818 | S | 10/2010 | Khalil |
| 7,985,222 | B2 | 7/2011 | Gall |
| 8,118,952 | B2 | 2/2012 | Gall |
| 8,231,629 | B2 | 7/2012 | Lerner |
| 8,267,975 | B2 | 9/2012 | McCombs |
| 8,491,583 | B2 | 7/2013 | Gall |
| D691,720 | S | 10/2013 | Cheney et al. |
| D693,929 | S | 11/2013 | Fagan |
| 8,623,060 | B2 | 1/2014 | Vlahos |
| 8,702,768 | B2 * | 4/2014 | Tipirneni ............. A61B 17/742 |
| | | | 606/320 |
| D705,930 | S | 5/2014 | Cheney |
| D706,927 | S | 6/2014 | Cheney et al. |
| D707,357 | S | 6/2014 | Cheney et al. |
| D717,951 | S | 11/2014 | Cheney et al. |
| 9,011,505 | B2 | 4/2015 | Prandi |
| 9,095,338 | B2 | 8/2015 | Taylor et al. |
| 9,113,976 | B2 | 8/2015 | Yevmenenko |
| 9,402,624 | B1 | 8/2016 | Scott et al. |
| D773,665 | S | 12/2016 | Cheney et al. |
| D773,666 | S | 12/2016 | Cheney et al. |
| D775,336 | S | 12/2016 | Shelton, IV et al. |
| D775,351 | S | 12/2016 | Agarwal |
| D777,329 | S | 1/2017 | Montoya et al. |
| D782,674 | S | 3/2017 | Nering et al. |
| 9,585,656 | B2 | 3/2017 | Taber et al. |
| 9,675,395 | B2 | 6/2017 | Averous et al. |
| D804,666 | S | 12/2017 | Guo et al. |
| 9,861,413 | B2 * | 1/2018 | Palmer ................ A61B 17/863 |
| D810,933 | S | 2/2018 | Chrisman |
| 9,901,338 | B2 | 2/2018 | Anderson |
| 10,085,743 | B2 | 10/2018 | Roedl et al. |
| 10,105,134 | B2 | 10/2018 | Biedermann et al. |
| 10,117,647 | B2 | 11/2018 | Cheney |
| D857,199 | S | 8/2019 | Cheney et al. |
| 10,383,625 | B1 | 8/2019 | Pirela-Cruz |
| 10,568,627 | B2 | 2/2020 | Guo et al. |
| 10,610,218 | B2 | 4/2020 | Palmer et al. |
| D883,482 | S | 5/2020 | Majors et al. |
| D886,299 | S | 6/2020 | Cundiff et al. |
| D891,618 | S | 7/2020 | Cheney |
| D895,113 | S | 9/2020 | Blair et al. |
| 10,863,982 | B2 | 12/2020 | Wahl |
| 11,179,149 | B2 | 11/2021 | Hartdegen et al. |
| D939,704 | S | 12/2021 | Bales |
| 11,291,488 | B1 | 4/2022 | OFlaherty et al. |
| 11,311,289 | B1 | 4/2022 | Ritz et al. |
| 11,317,951 | B2 | 5/2022 | Hollis et al. |
| 11,331,130 | B1 | 5/2022 | Lui et al. |

(56) References Cited

U.S. PATENT DOCUMENTS

| D960,371 S | 8/2022 | Hollis et al. |
| D961,081 S | 8/2022 | Sayger et al. |
| 11,523,820 B2 | 12/2022 | Cheney et al. |
| 11,642,124 B2 | 5/2023 | Maclure et al. |
| D988,856 S | 6/2023 | D'Ascanio et al. |
| D1,009,269 S | 12/2023 | Blair et al. |
| 11,911,025 B1 | 2/2024 | Blair et al. |
| D1,017,034 S | 3/2024 | Coyne et al. |
| D1,017,038 S | 3/2024 | Bushko et al. |
| 11,925,345 B2 | 3/2024 | Goldstein et al. |
| 11,937,808 B2 | 3/2024 | Campbell et al. |
| D1,025,358 S | 4/2024 | Blair et al. |
| 11,969,167 B2 | 4/2024 | Hartdegen et al. |
| D1,034,989 S | 7/2024 | Chevrel |
| 12,042,386 B2 | 7/2024 | Cheney et al. |
| D1,050,432 S | 11/2024 | Niver et al. |
| D1,050,433 S | 11/2024 | Reed et al. |
| 12,207,815 B1 | 1/2025 | Blair et al. |
| 2002/0055742 A1 | 5/2002 | Leiberman |
| 2002/0058949 A1 | 5/2002 | Iaia |
| 2003/0021655 A1 | 1/2003 | Correll et al. |
| 2003/0055314 A1 | 3/2003 | Petitto |
| 2003/0065332 A1* | 4/2003 | TenHuisen ............ A61F 2/0811 |
| | | 606/909 |
| 2004/0002710 A1 | 1/2004 | Han |
| 2004/0137033 A1* | 7/2004 | Calhoun ............... A61L 31/148 |
| | | 424/426 |
| 2004/0230193 A1 | 11/2004 | Cheung |
| 2005/0096656 A1 | 5/2005 | Behrens |
| 2005/0107791 A1 | 5/2005 | Manderson |
| 2005/0159749 A1 | 7/2005 | Levy |
| 2005/0277940 A1 | 12/2005 | Neff |
| 2006/0058802 A1 | 3/2006 | Kofoed |
| 2006/0064106 A1 | 3/2006 | Fernandez |
| 2006/0084980 A1 | 4/2006 | Melkent |
| 2006/0173461 A1 | 8/2006 | Kay |
| 2006/0200141 A1 | 9/2006 | Janna |
| 2006/0233628 A1 | 10/2006 | Lee |
| 2006/0264945 A1 | 11/2006 | Edidin |
| 2006/0264954 A1 | 11/2006 | Sweeney |
| 2007/0100342 A1 | 5/2007 | Green |
| 2007/0123873 A1 | 5/2007 | Czartoski |
| 2007/0260248 A1 | 11/2007 | Tipirneni |
| 2007/0270855 A1 | 11/2007 | Partin |
| 2007/0270906 A1 | 11/2007 | Molz |
| 2008/0147126 A1 | 6/2008 | Tipirneni |
| 2008/0147127 A1 | 6/2008 | Tipirneni |
| 2008/0161808 A1 | 7/2008 | Fox |
| 2008/0167666 A1 | 7/2008 | Fiere et al. |
| 2008/0234763 A1 | 9/2008 | Patterson et al. |
| 2008/0287949 A1 | 11/2008 | Keith |
| 2008/0300510 A1 | 12/2008 | Schwyn |
| 2008/0300597 A1 | 12/2008 | Morgan |
| 2008/0319443 A1 | 12/2008 | Focht et al. |
| 2009/0062800 A1 | 3/2009 | Shano |
| 2009/0105768 A1 | 4/2009 | Cragg |
| 2009/0149861 A1 | 6/2009 | Brodsky |
| 2009/0157123 A1 | 6/2009 | Appenzeller et al. |
| 2010/0010490 A1 | 1/2010 | Brigido |
| 2010/0063506 A1 | 3/2010 | Fox et al. |
| 2010/0076498 A1 | 3/2010 | Tyber et al. |
| 2010/0076503 A1 | 3/2010 | Beyar |
| 2010/0179551 A1 | 7/2010 | Keller |
| 2010/0268229 A1 | 10/2010 | Siravo |
| 2011/0004212 A1 | 1/2011 | Gall |
| 2011/0118842 A1 | 5/2011 | Bernard et al. |
| 2012/0316607 A1 | 12/2012 | Frenk |
| 2013/0030437 A1 | 1/2013 | Fox |
| 2013/0123863 A1 | 5/2013 | Hollis et al. |
| 2013/0184768 A1 | 7/2013 | McIff et al. |
| 2013/0267956 A1 | 10/2013 | Terrill et al. |
| 2013/0338669 A1 | 12/2013 | Brianza |
| 2014/0018809 A1 | 1/2014 | Allen |
| 2014/0031794 A1 | 1/2014 | Windolf |
| 2014/0228845 A1 | 8/2014 | Gorsline |
| 2014/0276830 A1 | 9/2014 | Cheney |
| 2014/0277516 A1 | 9/2014 | Miller et al. |
| 2015/0282819 A1 | 10/2015 | Austin et al. |
| 2015/0313592 A1 | 11/2015 | Coillard-Lavirotte et al. |
| 2016/0000434 A1 | 1/2016 | Cocaign et al. |
| 2016/0030039 A1 | 2/2016 | Seavey et al. |
| 2016/0066907 A1 | 3/2016 | Cheney et al. |
| 2016/0199060 A1 | 7/2016 | Morgan et al. |
| 2016/0213412 A1 | 7/2016 | Palmer |
| 2016/0235460 A1 | 8/2016 | Wahl |
| 2017/0181779 A1 | 6/2017 | Leither et al. |
| 2017/0196608 A1 | 7/2017 | Castaneda |
| 2017/0202552 A1 | 7/2017 | Coleman et al. |
| 2017/0348037 A1 | 12/2017 | Sexson |
| 2017/0360489 A1* | 12/2017 | Palmer ............... A61B 17/7225 |
| 2018/0092677 A1 | 4/2018 | Peterson |
| 2018/0263669 A1 | 9/2018 | Peterson et al. |
| 2019/0000451 A1 | 1/2019 | Majors et al. |
| 2019/0046182 A1 | 2/2019 | Krumme |
| 2019/0105040 A1 | 4/2019 | Gordon |
| 2019/0117219 A1 | 4/2019 | Ritz et al. |
| 2019/0133657 A1 | 5/2019 | Orbay |
| 2019/0150921 A1 | 5/2019 | Fonte et al. |
| 2019/0154070 A1 | 5/2019 | Kargenian et al. |
| 2019/0192140 A1 | 6/2019 | Ducharme et al. |
| 2019/0192160 A1 | 6/2019 | Stamp |
| 2019/0357951 A1 | 11/2019 | Rogers |
| 2020/0000465 A1 | 1/2020 | Maclure et al. |
| 2020/0008807 A1 | 1/2020 | Hollis |
| 2020/0038076 A1 | 2/2020 | Amis et al. |
| 2020/0038080 A1 | 2/2020 | Palmer et al. |
| 2020/0197005 A1 | 6/2020 | Daniel |
| 2020/0229813 A1 | 7/2020 | Seykora et al. |
| 2021/0068822 A1 | 3/2021 | Wahl |
| 2022/0117599 A1 | 4/2022 | Fein et al. |
| 2022/0280197 A1 | 9/2022 | Blair |
| 2022/0338869 A1 | 10/2022 | Kobayashi |
| 2023/0000488 A1 | 1/2023 | Palmer et al. |
| 2023/0172647 A1 | 6/2023 | Knight et al. |
| 2023/0200809 A1 | 6/2023 | Wahl |
| 2023/0258214 A1 | 8/2023 | Wang |
| 2023/0270435 A1 | 8/2023 | Fox |
| 2023/0346369 A1 | 11/2023 | Bushko et al. |
| 2024/0099715 A1 | 3/2024 | Blair et al. |
| 2024/0180600 A1 | 6/2024 | Taylor et al. |

FOREIGN PATENT DOCUMENTS

| CA | 132677 S | 6/2010 |
| CN | 2472682 Y | 1/2002 |
| CN | 303149448 S | 4/2015 |
| CN | 304907199 S | 11/2018 |
| CN | 306788209 S | 8/2021 |
| DE | 19708279 | 9/1998 |
| FR | 19852850001 S1 | 2/1986 |
| FR | 2874166 B1 | 3/2012 |
| FR | 3008302 B1 | 12/2016 |
| GB | 1035018 A | 7/1966 |
| GB | 6352634 S | 3/2024 |
| GB | 6352635 S | 3/2024 |
| IN | 256120 S | 6/2014 |
| JP | D1083812 S | 9/2000 |
| JP | D1132991 S | 2/2002 |
| JP | D1504138 S | 8/2014 |
| KR | 300967753 S | 8/2018 |
| WO | 199524870 | 9/1995 |
| WO | 2005094705 | 10/2005 |
| WO | 2015014771 | 2/2015 |
| WO | 2015026357 A1 | 2/2015 |
| WO | 2017207922 A1 | 12/2017 |
| WO | 2019226248 A1 | 11/2019 |
| WO | 2022010920 A1 | 1/2022 |

OTHER PUBLICATIONS

Extended European Search Report dated Mar. 4, 2010 for European Pat. Appl. No. 06758489.6.

(56)                     References Cited

OTHER PUBLICATIONS

Ankle Arthrodesis Nail Surgical Technique, pp. 1-16, BioMet, Inc., Warsaw, Indiana, USA, 2000.

Panta Arthrodesis Nail Surgical Technique brochure, pp. 1-23, Integra Lifosciences Corporation, Plainsboro, New Jersey.

Retro Nail Ankle Arthrodesis treats arthritic deformity, factures, failed fusion, retrieved from the Internet Apr. 4, 2007 at http://www.orthofix.com/products/retronail.asp?cid=5, © 2007 orthofix.com.

T2 Tibial Nailing System, Operative Technique, pp. 1-31, Stryker Trauma GmbH, Germany, 2004.

Tibiotalocalcaneal Fusion Using the VersaNail, Surgical Technique, pp. 1-15, DePuy Orthopaedics, Inc., Warsaw, Indiana, USA, 2002.

Versanail tTC, Surgical Technique Tibiotalocalcaneal Nailing System Options Made Easy, pp. 1-19, Trauma & Extremities Group, DePuy, a Johnson & Johnson Company, 2006.

Andreasen et al., Laboratory and Clinical Analyses of Nitinol Wire, American Journal of Orthepedics, vol. 73, No. 2, 1978, pp. 142-151.

Barbella, Michael, "Enovis Expands DynaClip Family With Debut of New Staples. The procedure-specific staples combine strength with sustained dynamic compression for mid-foot and first MTP joint fusions." Retrieved from the Internet: https://www.odtmag.com/breaking-news/enovis-expands-dynaclip-family-with-debut-of-new-staples/, Jan. 17, 2023, 27 pages.

International Search Report received for PCT Application No. PCT/US06/15207, mailed on Aug. 18, 2006, 2 pages.

Cragg et al., A New Percutaneous Vena Cava Filter, American Journal of Roentgenology, vol. 141, 1983, pp. 601-604.

DePuy Synthes, BME Elite Continuous Compression Implant Product Overview. DePuy Synthes, Pamphlet, 2017, 4 pages.

El Feninat, et al., "Shape Memory Materials for Biomedical Applications", Advanced Engineering Materials, vol. 4, No. 3, 2002, pp. 91-104.

Gall et al., Shape-Memory Polymers for Microelectromechanical Systems, Journal of Microelectromechanical Systems, vol. 13, No. 3, Jun. 2004, pp. 472-483.

Gall et al., Shape memory polymer nanocomposites, Acta Materialia, vol. 50, 2002, pp. 5115-5126.

Gall et al., Thermomechanics of the shape memory effect in polymers for biomedical applications, Journal of Biomedical Materials Research, 2005 vol. 73A, pp. 339-348.

International Search Report and Written Opinion received for PCT Patent Application No. PCT/US2023/075457, mailed on Feb. 14, 2024, 14 pages.

International Search Report and Written Opinion received for PCT Patent Application No. PCT/US2024/030224, mailed on Sep. 3, 2024, 12 pages.

Jeon et al., Shape memory and nanostructure in poly(norbornyl-POSS) copolymers, Polymer International, vol. 49, 2000, pp. 453-457.

Langer et al., Designing materials for biology and medicine, Nature, vol. 428, Apr. 1, 2004, pp. 487-492.

Lendlein, Andreas et al., AB-polymer networks based on oligo (ε-caprolactone) segments showing shape-memory properties, PNAS, vol. 98, No. 3, Jan. 30, 2001, pp. 842-847.

Lendlein et al., Biodegradable, Elastic Shape-Memory Polymers for Potential Biomedical Applications, Science, vol. 296, May 31, 2002, pp. 1673-1676.

Lendlein et al., Light-induced shape-memory polymers, Nature, vol. 434, Apr. 14, 2005, pp. 879-882.

Lin et al., Study on Shape-Memory Behavior of Polyether-Based Polyurethanes. I. Influence of the Hard-Segment Content, Journal of Applied Polymer Science, vol. 69, 1998, pp. 1563-1574.

Lin et al., Study on Shape-Memory Behavior of Polyether-Based Polyurethanes. II. Influence of Soft-Segment Molecular Weight, Journal of Applied Polymer Science, vol. 69, 1998, pp. 1575-1586.

Liu et al., Chemically Cross-Linked Polycyclooctene: Synthesis, Characterization, and Shape Memory Behavior, Macromolecules, vol. 35, 2002, pp. 9868-9874.

Liu et al., Thermomechanics of shape memory polymers: Uniaxial experiments and constitutive modeling, International Journal of Plasticity, vol. 22, 2006, pp. 279-313.

Liu et al., Thermomechanical recovery couplings of shape memory polymers in flexure, Institute of Physics Publishing, Smart Materials and Structers, vol. 12, 2003, pp. 947-954.

Maitland et al., Photothermal Properties of Shape Memory Polymer Micro-Actuators for Treating Stroke, Lasers in Surgery and Medicine, vol. 30, 2002, pp. 1-11.

MedShape Inc., "MedShape Launches the DynaClip Forte NiTiNOL Bone Fixation System. The four-leg design is indicated for Lapidus fusion and other demanding applications." ODT, Retrieved from the Internet: https://www.odtmag.com/breaking-news/medshape-launches-the-dynaclip-forte-nitinol-bone-fixation-system/, Sep. 10, 2020, 17 pages.

Metcalfe et al., Cold hibernated elastic memory foams for endovascular interventions, Biomaterials vol. 24, 2003, pp. 491-497.

Metzger et al., Mechanical Properties of Mechanical Actuator for Treating Ischemic Stroke, Biomedical Microdevices, vol. 4, No. 2, May 2002, pp. 89-96.

Smith et al., Time and Temperature Dependence of the Ultimate Properties of an SER Rubber at Constant Elongations, Journal of Applied Physics, vol. 31, No. 11, Nov. 1960, pp. 1892-1898.

Smith, Thor L., Strength of Elastomers—A Perspective, Polymer Engineering and Science, vol. 17, No. 3, 1977, pp. 129-143.

Smith, Thor L., Ultimate Tensile Properties of Elastomers. I. Characterization by a Time and Temperature Independent Failure Envelope, Journal of Polymer Science: Part A, vol. 1, No. 12, 1963, pp. 3597-3615.

Stryker EasyClip Osteosynthesis Compression Staples. Stryker GMBH, Switzerland, Pamphlet, 2015, 20 pages.

Takahashi et al., Structure and Properties of Shape-Memory Polyurethane Block Copolymers, Journal of Applied Polymer Science, vol. 60, 1996, pp. 1061-1069.

Tobushi et al., Thermomechanical Constitutive Modeling in Shape Memory Polymer of Polyurethane Series, Journal of Intelligent Material Systems and Structures, vol. 8, 1997, pp. 711-718.

Tobushi et al., Thermomechanical properties in a thin film of shape memory polymer of polyurethane series, Smart Materials and Structure, vol. 5, 1996, pp. 483-491.

Wache et al., Development of a polymer stent with shape memory effect as a drug delivery system, Journal of Materials Science: Materials in Medicine, vol. 14, 2003, pp. 109-112.

Wasilewski, R., Stress-Assisted Martensite Formation in TiNi Scripta Metallurgica, vol. 5, No. 2, 1971, pp. 127-130.

Watanabe, K., Studies on New Superelastic NiTi Orthodontic Wire (Part 1) Tensile and Bend Test, Journal of Japan Society Dental Apparatus and Materials, vol. 23, No. 61, 1982, pp. 1-61.

Wright, Fuseforce Fixation System Surgical Technique. Wright Medical Group N.V., Pamphlet, Oct. 25, 2018, 8 pages.

Yahia, L., (Ed.), Shape Memory Implants, Springer-Verlag Berlin Heidelberg New York, 2000, (complete book—out of print), 186 pages.

Yakacki et al., Strong and Biocompatible Shape Memory Polymers for Soft Tissue Orthopedic Fixation, Nature Materials, 2006, pp. 1-23.

Zhu et al., Shape-Memory Effects of Radiation Crosslinked Poly(ε-caprolactone), Journal of Applied Polymer Science, vol. 90, 2003, pp. 1589-1595.

* cited by examiner

700

703

707

701

706

705

704

RESORPTION-CONTROLLED COMPRESSION DEVICES AND PROCESSES FOR MAKING AND USING THE SAME

CROSS-REFERENCE TO RELATED APPLICATIONS

This application is a continuation of U.S. patent application Ser. No. 17/685,163, filed on Mar. 2, 2022, titled "RESORPTION-CONTROLLED COMPRESSION DEVICES AND PROCESSES FOR MAKING AND USING THE SAME," which claims the benefit of and priority to U.S. Provisional Patent Application No. 63/155,322, filed Mar. 2, 2021, titled "RESORPTION-CONTROLLED COMPRESSION DEVICES AND PROCESSES FOR MAKING AND USING THE SAME." The entire disclosures of these applications are incorporated herein by reference in their entireties.

TECHNICAL FIELD

The present systems and processes relate generally to resorption-activated compression of biological structures, such as bones and bony fragments.

BACKGROUND

Previous compression devices typically apply compressive forces upon installation to induce bone growth between two or more bony fragments. For example, upon being disengaged from an insertion tool, a previous compression device automatically engages a compression element and the compressive force is immediately applied at the implantation site. However, in many patients it may be advantageous to delay the initialization of compression. For example, it may be advantageous to treat comminuted fractures (e.g., where a bone is separated into three or more pieces) with an initial period of bone fixation before compression is applied. In previous instances, providing fixation and compression to a comminuted fracture may require two or more surgeries, a fixation surgery to fixate the bony fragments and a compression surgery to compress the fixated bony fragments. The additional required complexity and surgical intervention may increase the cost of care and may compound the total risk of treating the injury, for example, due to the increased amount cuts and anesthesia used to perform the surgeries.

Therefore, there exists a long-felt, but unmet need for a compression device that allows for a controlled, delayed activation of compressive forces.

BRIEF SUMMARY OF THE DISCLOSURE

Briefly described, and according to one embodiment, aspects of the present disclosure generally relate to devices for providing resorption-controlled compression and processes for making and using the same.

In various embodiments, a delayed compression device includes at least one resorbable element that, upon being resorbed by the body following device implantation, results in the activation of at least one compression element. As used herein, resorption generally refers to processes in which the human body (e.g., or other creature) absorbs an implanted or deposited material, for example, via natural enzymatic and hydrolytic mechanisms. In various embodiments, the at least one resorbable element described herein may include one or more resorbable materials including, but not limited to, PDLG (e.g., copolymer of DL-lactide and Glycolide with a 50/50 molar ratio). PLG (e.g., copolymer of L-lactide and Glycolide with a 10/90 molar ratio of L-lactide to Glycolide), poly alpha hydroxy esters (e.g., including, but not limited to, polycaprolactone, PLLA, POLA, PGA, POLA, and/or a mixture of any of the previous), poly beta amino esters, poly anhydrides, poly dioxanone (PDO), biodegradable iron (Fe), and/or biodegradable magnesium (Mg). According to one embodiment, the at least one resorbable element delays compression by functioning as a physical barrier preventing the compression element from compressing at least two anchors together, which shields bone fragments (or other suitable body parts) from compressive stress. In various embodiments, the anchors are attached to separate bone fragments (e.g., or other suitable body parts and/or medical devices, such as other implanted devices), for delayed compression between the separate bone fragments. In some embodiments, the anchors may attach to the separate bone fragments via a screw, nail, staple, and/or another attachment method. In one or more embodiments, the compression element may include one or more compression materials that has a quality of compressing after being deformed past an elongation point. In at least one embodiment, the one or more compression materials may include nitinol.

In various embodiments, the resorbable element includes one or more shapes including, but not limited to, cylinders, rings, spheres, ovoids, wedges, and shim shapes. In one or more embodiments, the resorption rate of the resorbable element is proportional to the level of surface area of the element that is exposed to the body upon implantation.

In some embodiments, the choice of material of the resorbable element may also affect the resorption rate. In at least one embodiment, the choice of material of the resorbable element may affect the resorption rate more than the level of surface area of the resorbable element that is exposed to the body upon implantation. In at least one embodiment, the one or more resorbable element shapes include features to modify the exposed surface area thereof and thus support a desired resorption rate. In one or more embodiments, the features for surface area modification include, but are not limited to, grooves, pores, voids, and other structures configured to increase or decrease the exposed surface area of a resorbable element shape. For example, in at least one embodiment, the at least one resorbable element may include a plurality of grooves to increase an exposed surface area thereof and, thereby, increase the resorption rate of the resorbable element.

In various embodiments, the delayed compression device may include two or more anchors, at least one resorbable element, and at least one compression element that is operatively connected to each of the anchors. In one or more embodiments, the at least one resorbable element delays compression by functioning as a physical barrier, preventing the transfer of the compressive force from the compression element to the anchors. In one or more embodiments, as the at least one resorbable element is resorbed into the body, the compressive force from the compression element is transferred from the at least one resorbable element to the anchors, causing the anchors, and thus the attached body parts, to compress. In at least one embodiment, the at least one resorbable element includes a sleeve of a predetermined thickness sufficient to resist the compressive load of the compression element. In many embodiments, by providing specific ratios of implant thickness and exposed surface area, the at least one resorbable element is configured to provide sufficient resilience to compressive loads for a predetermined time period.

According to one embodiment, the delayed compression device may also include a sliding element that is connected to one of the anchors and encircles the compression element. In at least one embodiment, the sliding element may protrude from one of the anchors and, upon the resorption of the resorbable element, may translate or slide towards the opposing anchor.

According to a first aspect, a medical device comprising: A) a first anchor for attachment to a first bone fragment; B) a second anchor coupled to the first anchor via a compression element, the second anchor for attachment to a second bone fragment; C) the compression element comprising nitinol and attached to the first anchor and the second anchor, the compression element deformed to a deformed position; and D) a resorbable element holding the compression element in the deformed position, wherein: 1) the resorbable element comprises a material, size, and shape such that the resorbable element resorbs in a predetermined amount of time after insertion into a patient; and 2) after the predetermined amount of time following insertion into the patient, the resorbable element is resorbed and the compression element moves from the deformed position to a non-deformed position compressing the first bone fragment and the second bone fragment.

According to a second aspect, the medical device of the first aspect or any other aspect, wherein the predetermined amount of time comprises about 2-8 weeks.

According to a third aspect, the medical device of the second aspect or any other aspect, wherein the shape of the resorbable element is a sleeve-like shape.

According to a forth aspect, the medical device of the third aspect or any other aspect, wherein the first anchor comprises screw threads.

According to a fifth aspect, the medical device of the fourth aspect or any other aspect, wherein the resorbable element comprises one or more of the following materials: A) DL-lactide and Glycolide with a 50/50 molar ratio; B) L-lactide and Glycolide with a 10/90 molar ratio of L-lactide to Glycolide; C) poly alpha hydroxy esters; D) poly beta amino esters; E) poly anhydrides, poly dioxanone (PDO); F) biodegradable iron (Fe); and/or G) biodegradable magnesium (Mg).

According to a sixth aspect, a medical device comprising: A) a first anchor for attachment to a first bone fragment; B) a second anchor coupled to the first anchor via a compression element, the second anchor for attachment to a second bone fragment; C) the compression element between the first anchor and the second anchor, and D) a resorbable element maintaining the first anchor and the second anchor at a first distance, wherein: 1) the resorbable element is configured to at least partially resorb after insertion into a patient; and 2) after the resorbable element is at least partially resorbed, the compression element forces the first anchor and/or the second anchor to translate such that the first anchor and the second anchor are at a second distance, thereby compressing the first bone fragment and the second bone fragment.

According to a seventh aspect, the medical device of claim 6, wherein the resorbable element comprises one or more materials from the group comprising: DL-lactide and Glycolide with a 50/50 molar ratio, L-lactide and Glycolide with a 10/90 molar ratio of L-lactide to Glycolide, poly alpha hydroxy esters, poly beta amino esters, poly anhydrides, poly dioxanone (PDO), biodegradable iron (Fe), and biodegradable magnesium (Mg).

According to an eighth aspect, the medical device of claim 6, wherein: A) the medical device comprises a midpoint between the first anchor and the second anchor, and B) after the resorbable element is at least partially resorbed, the compression element forces the first anchor and/or the second anchor to translate toward the midpoint.

According to a ninth aspect, the medical device of claim 8, wherein the resorbable element is between the first anchor and the second anchor.

According to a tenth aspect, the medical device of claim 9, wherein the resorbable element is sleeve-like in shape.

According to an eleventh aspect, the medical device of claim 10, wherein the compression element passes through the resorbable element.

According to a twelfth aspect, the medical device of the sixth aspect or any other aspect, wherein: A) the second anchor is coupled to the compression element at a first side of the second anchor, and B) the resorbable element is coupled to the compression element at a second side of the second anchor, the second side of the second anchor opposite the first side of the second anchor.

According to a thirteenth aspect, the medical device of the sixth aspect or any other aspect, wherein the medical device is a screw.

According to a fourteenth aspect, the medical device of the sixth aspect or any other aspect, wherein the medical device is an intramedullary nail.

According to a fifteenth aspect, a method comprising: A) coupling a first anchor of a medical device to a first bone fragment within a patient; B) coupling a second anchor of the medical device to a second bone fragment within the patient; and C) positioning the first bone fragment adjacent to the second bone fragment in a first position, wherein: 1) the first anchor is coupled to the second anchor by a compression element; 2) the first anchor and the second anchor are held in a fix position via a resorbable element; and 3) upon at least partial resorption of the resorbable element, the first anchor and/or the second anchor translate toward a midpoint of the medical device via the compression element, thereby moving the first bone fragment and the second bone fragment to a second position and compressing the first bone fragment and the second bone fragment.

According to a sixteenth aspect, the method of the fifteenth aspect or any other aspect, wherein in the first position, the first bone fragment and the second bone fragment are uncompressed.

According to a seventeenth aspect, the method of the sixteenth aspect or any other aspect, wherein in the first position, the first bone fragment and/or the second bone fragment experience micro-motion.

According to an eighteenth aspect, the method of the seventeenth aspect or any other aspect, wherein the resorbable element comprises one or more materials from the group comprising: DL-lactide and Glycolide with a 50/50 molar ratio, L-lactide and Glycolide with a 10/90 molar ratio of L-lactide to Glycolide, poly alpha hydroxy esters, poly beta amino esters, poly anhydrides, poly dioxanone (PDO), biodegradable iron (Fe), and biodegradable magnesium (Mg).

According to a nineteenth aspect, the method of the eighteenth aspect or any other aspect, wherein the resorbable element is between the first anchor and the second anchor.

According to a twentieth aspect, the method of the nineteenth aspect or any other aspect, wherein the compression element comprises nitinol.

These and other aspects, features, and benefits of the claimed devices and process(es) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
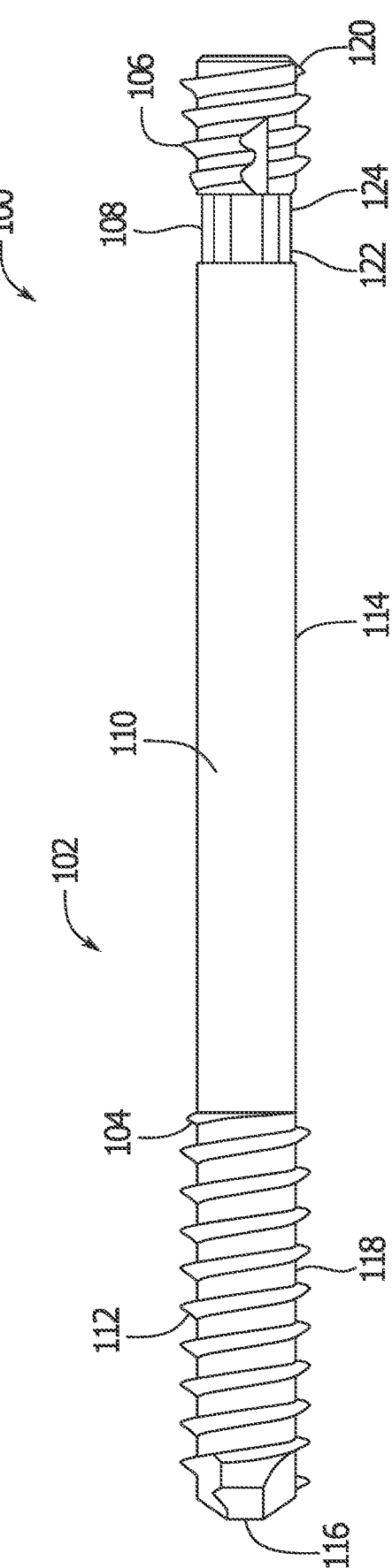
FIG. 1 is a perspective view of an exemplary compression device according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

As used herein, "resorbable" generally refers to a quality of being capable of breaking down over time in an in vivo environment as a result of biological mechanisms, such as, for example, enzymatic processes.

As used herein, "bone fragment" can refer to any bone or any portion of a bone.

Overview

Aspects of the present disclosure generally relate to devices for providing resorption-controlled compression and processes for making and using the same.

In one or more embodiments, a delayed compression device for resorption-controlled compression includes one or more resorbable elements. In at least one embodiment, the resorbable element inhibits a compression response of the delayed compression device until the resorbable element is sufficiently bio-resorbed in an in vivo environment (e.g., an implant site). In various embodiments, the resorbable element is configured to be resorbed at a predetermined rate such that compression is initiated at a predetermined post-implantation time period. According to one embodiment, one or more properties and parameters of the resorbable element are selected to provide a desired resorption-compression response (e.g., also referred to herein as "resorption rate"). In at least one embodiment, the one or more properties and parameters of the resorbable element include, but are not limited to, dimensions of the resorbable element (e.g., length, height, width, depth, and/or surface area), one or more shapes of the resorbable element, one or more resorbable materials forming the resorbable element, a quantity of resorbable elements provided in a system or device (e.g., 1, 2, 3, or any suitable number of resorbable elements), and an arrangement or configuration of one or more resorbable elements. In one or more embodiments, the resorbable element described herein may include one or more resorbable materials including, but not limited to, PDLO (e.g., copolymer of DL-lactide and Olycolide with a 50/50 molar ratio), PLO (e.g., copolymer of L-lactide and Olycolide with a 10/90 molar ratio of L-lactide to Olycolide), poly alpha hydroxy esters (e.g., including, but not limited to, poly-caprolactone, PLLA, PDLA, POA, POLA, and/or a mixture of any of the previous), poly beta amino esters, poly anhydrides, poly dioxanone (PDO), biodegradable iron (Fe), and/or biodegradable magnesium (Mg).

In one or more embodiments, the resorbable element includes one or more shapes including, but not limited to, cylinders, rings, spheres, ovoids, wedges, and shim shapes that may prevent the delayed compression device from compressing. In one or more embodiments, one or more features for controlling surface area may be formed into the at resorbable element including, but not limited to, grooves, pores, voids, and other structures configured to increase or decrease the exposed surface area of the resorbable element.

In various embodiments, the delayed compression device includes, but is not limited to, one or more anchors, one or more compression elements, and one or more resorbable elements. The compression element can include a first end and a second end opposite the first end. In various embodiments, the first end and the second end are each attached to a different anchor. In at least one embodiment, the resorbable element maintains the compression element at a first distance between each anchor. In various embodiments, following at least partial resorption of the resorbable element, the compression element may compress to a second distance (e.g., less than the first distance), thereby forcing a first attached anchor toward a second attached anchor, or vice versa, or simultaneously forcing first and second attached anchors toward each other. In at least one embodiment, as the compression element moves from the deformed position to the non-deformed position, a distance between the first and second anchors decreases. In various embodiments, the first anchor and the second anchor are each attached to a different bone fragment and, thus, movement of the first and second anchors from a first distance to a second, lesser distance causes compression of the bone fragments. In other words, in at least one embodiment, the resorbable element is configured to hold a first anchor and a second anchor at a fixed position. In at least one embodiment, following partial or total resorption of the resorbable element, the compression element is configured to force the first anchor and the second anchor toward a second position that may include a midpoint between the first anchor and the second anchor, a point closer to the first anchor, or a point closer to the second anchor.

In one or more embodiments, each of the anchors may be attached separately to at least two bone fragments (e.g., or other body parts, or external and/or internal medical devices). In many embodiments, the anchors may be in the form of screws, nails, staples, or other attachment mechanisms. In at least one embodiment, the compression element has two ends, and each of the two ends of the compression element are operatively connected separately to each of the anchors such that the anchors are operatively connected via the compression element.

In one or more embodiments, the resorbable element is configured such that the resorbable element bears a compressive load being supplied by the compression element. In one or more embodiments, the compression element may include one or more compression materials having a compression or contracting quality such that the compression material, when deformed or stretched, may compress or contract back to a pre-determined length or shape. In many embodiments, the compression material may include nitinol. In some embodiments, the resorbable element is configured to limit or inhibit the compression element from compressing. In at least one embodiment, the resorbable element may encompass the compression element such that the resorbable element prevents the compression element from compressing or contracting until the resorbable element begins to be resorbed.

In various embodiments, upon implantation of the delayed compression device, a first anchor of the anchors is connected to a first bone fragment of the bone fragments, and a second anchor of the anchors, opposite the first anchor thereof, is connected to a second bone fragment of the bone fragments. In many embodiments, prior to activation of compression via resorption, the delayed compression device fixates the first and second bone fragments. According to one embodiment, the resorbable element is resorbed over a period of time, the one or more embodiments, the resorbable element may be resorbed to a point in which the resorbable element may no longer prevent the compressive force from transferring from the resorbable element to the first and second bone fragments. In some embodiments, when the resorbable element no longer prevents the transfer of compressive force, the two anchors, via the sliding element, may translate towards each other. For example, in at least one embodiment, the resorbable element may be resorbed to the point at which the compressive forces cause the resorbable element to break, and the compressive forces transfer from resorbable element to the anchors all at once.

According to a further embodiment, as the resorbable element may be tuned so that the resorbable element is resorbed over a predetermined time period (e.g., 2-8 weeks, 1-2 months, 3 months, or any suitable time period), such that the compressive force experienced by first and second bone fragments gradually increases until the resorbable element is substantially completely resorbed. For example, in at least one embodiment, the resorbable element may be tuned so that the resorbable element is resorbed from the outer edges of the resorbable element towards the middle of the resorbable element. In this embodiment, the compression element compresses or contracts, causing the first anchor or the second anchor of the anchors to translate towards the opposing anchor in response to the compressive force of the compression element. In at least one embodiment, as the resorbable element is resorbed, the compressive force is transferred from the resorbable element to the anchors, and thus, the bone fragments, thereby providing continuous and sustained compression between the at least two body parts.

According to one embodiment, the compression is continuously applied until the compression element is fully contracted to a pre-stretch length.

Exemplary Embodiments

Figures 2A, 2B:
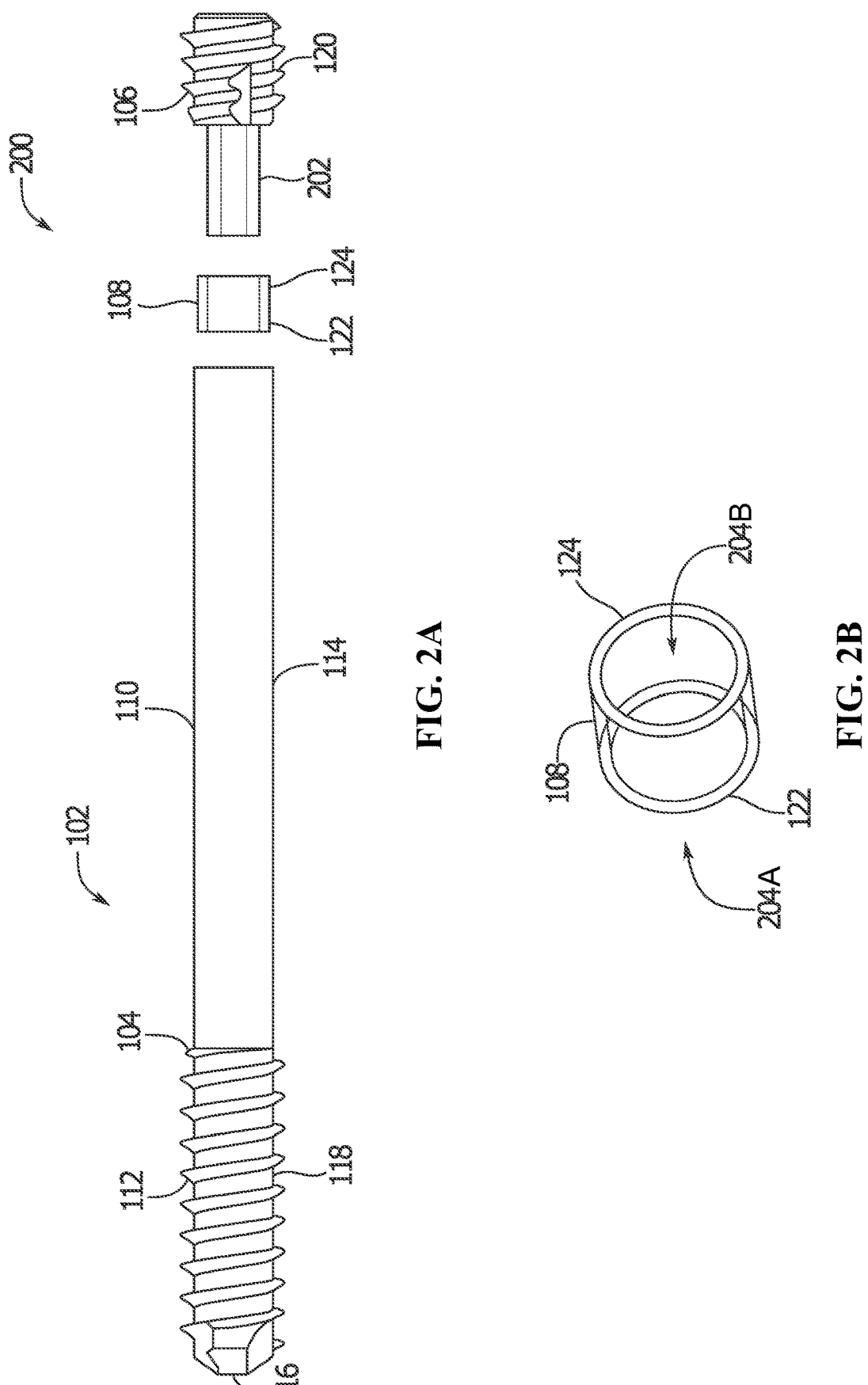
FIG. 2A is an assembly view of an exemplary compression device according to one embodiment of the present disclosure.
FIG. 2B is a perspective view of an exemplary resorbable element, according to one embodiment of the present disclosure.
Figure 3:
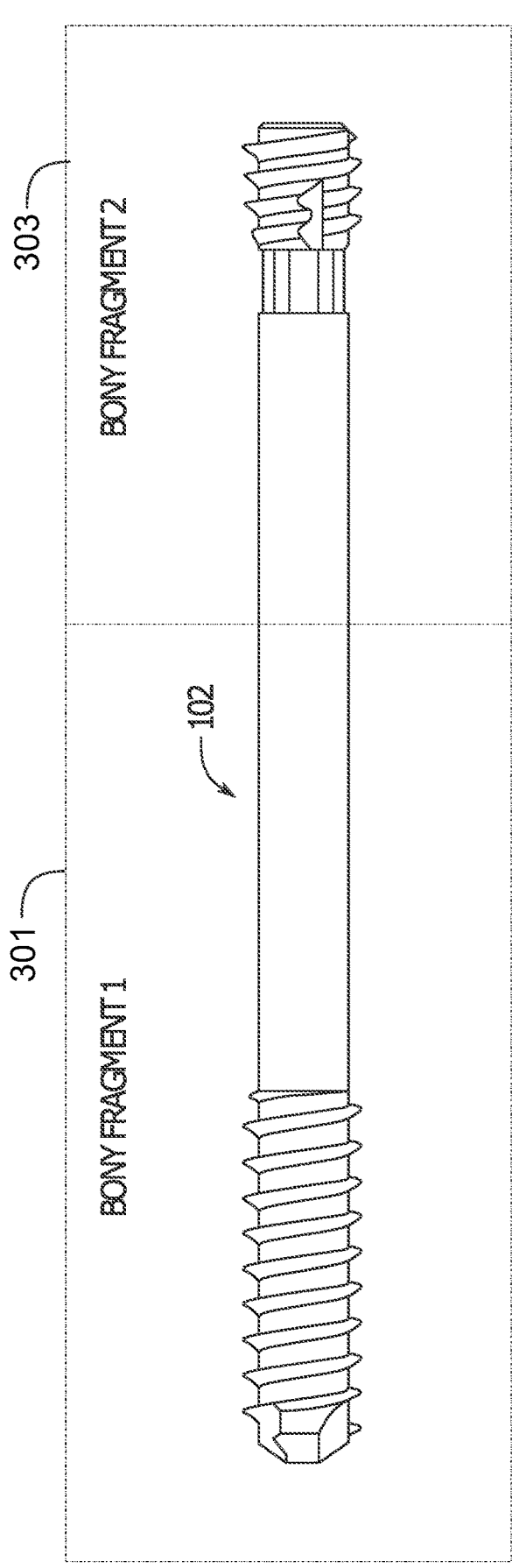
FIG. 3 is a side view of an exemplary compression device showing connection to bone fragments, according to one embodiment of the present disclosure.

Referring now to the figures, for the purposes of example and explanation of the fundamental processes and components of the disclosed systems and processes, reference is made to FIGS. 1-7, which illustrate views of exemplary delayed compression devices and processes associated therewith according to one embodiment of the present disclosure. Further information and technical details regarding an exemplary compression device can be found in U.S. application Ser. No. 17/184,104, filed Feb. 24, 2021, entitled "DYNAMIC COMPRESSION DEVICES AND PROCESSES FOR MAKING AND USING SAME," the disclosure of which is incorporated herein by reference in its entirety. As will be understood and appreciated, the delayed compression device 102 shown in FIGS. 1, 2, and 3 represents merely one approach or embodiment of the present system, and other aspects are used according to various embodiments of the present system.

In at least one embodiment, the delayed compression device 102 may fixate at least two bone fragments (see FIG. 3, body parts not shown) and apply a compressive force to the at least two body parts. In various embodiments, the at least two body parts may be bone fragments, connective tissue, or any injured other body part, and the compressive force applied by the delayed compression device 102 may increase healing speed and strength for the injury. In one or more embodiments, the delayed compression device 102 includes a first anchor 104, a second anchor 106, at least one resorbable element 108, and at least one compression element (not shown). In at least one embodiment, the compression element may include a first end, a second end, and a middle body connecting the first end and the second end.

In various embodiments, the first anchor 104 may be a hollow, substantially cylindrical body, comprising an exterior surface and an interior surface. In many embodiments, the first anchor 104 may further include a first portion 112 including a screw tip 116 for screwing into a body pa.it and screw threads 118 on the exterior surface of the first anchor 104 and a substantially smooth second portion 110. In some embodiments, the first anchor 104 may also include a second end 114. In one or more embodiments, the first anchor 104 may be operatively connected to a first end of the compression element (not shown in FIG. 1).

In various embodiments, the first anchor may have a length of 40 to 140 millimeters. In one or more embodiments, the length of the first end of the first anchor, including the screw tip and screw threads, is a length of about 19.271 millimeters. In one or more embodiments, the inside diameter of the cylindrical body of the first anchor may be about 2.6 millimeters, and the outside diameter of the cylindrical body of the first anchor may be about 4.75 millimeters. In at least one embodiment, the tapered portion of the second end of the first anchor may be about 10 millimeters in length and have an outside diameter of about 6.15 millimeters at the end furthest from the first end of the first anchor.

In one or more embodiments, the second end 114 may be hollow in order to accept a sliding element 202 (see FIG. 2A) operatively connected to (e.g., or otherwise attached to) the second anchor 106. In many embodiments, the second end 114 may define a circular opening (not shown) having a certain interior diameter capable of accepting the sliding element 202. In at least one embodiment, the opening defined by the second end 114 may access the hollow interior of the first anchor 104 such that the compression element may pass through the hollow interior of the first anchor 104. In at least one embodiment, the interior surface of the first anchor 104 may include screw threads, and the first end of the compression element may include screw threads, such that the screw threads of the first end of the compression element may be screwed into the screw threads on the interior surface of the first anchor 104. In one or more embodiments, the first anchor 104 may substantially surround the compression element.

In various embodiments, the second anchor 106 may include a threaded portion 120 and a sliding element 202 (see FIG. 2A). In many embodiments, the second anchor 106 may also include a hollow interior area (e.g., including through the sliding element 202) and an exterior surface. In at least one embodiment, the threaded portion 120 may be substantially cylindrical, having an outside diameter approximately equal to or greater than the diameter of the resorbable element 108. In many embodiments, the threaded portion 120 is on the exterior surface of the second anchor 106, for the purposes of screwing the second anchor 106 into a second body part. In some embodiments, the second anchor 106 may define a circular opening such that the second end of the compression element may pass through the hollow interior of the second anchor 106 via the opening in the second anchor 106. In at least one embodiment, the interior surface of the second anchor 106 may include screw threads, and the second end of the compression element may include screw threads, such that the screw threads on the second end of the compression element may be screwed into the screw threads on the interior surface of the second anchor 106. In at least one embodiment, the sliding element 202 may be sized such that the sliding element 202 of the second anchor 106 may fit inside the opening of the second end 114 of the first anchor 104.

In various embodiments, the second anchor may have length of about 19 millimeters, inclusive of the threaded portion and the sliding element 202. In many embodiments, the threaded portion may have a length of about 9 millimeters and the sliding element may have a length of about 10 millimeters. In one or more embodiments, the threaded portion may have a diameter of about 8 millimeters from the apex of the threads and a diameter of about 6.5 millimeters from the troughs of the threads.

In a further embodiment, the second end 114 of the first anchor 104 may be tapered outwards, such that the tapered portion may more easily accept the sliding element 202. In at least one embodiment, the second end 114 may include a first diameter that is approximately 6.150 millimeters, and a second diameter that is approximately 4.750 millimeters, and a tapered length that may be approximately 10.0 millimeters long. In another embodiment, the tapered length may be longer or shorter, depending on the overall length of the device 102.

In at least one embodiment, in order to operatively connect the second end of the compression element to the second anchor 106, the compression element passes through the sliding element 202 and may thereafter screw or otherwise operatively connect to the second anchor 106.

In various embodiments, the compression element may be 30 to 120 millimeters in length. In one or more embodiments, the width of the threads at each of the first end and the second end of the compression element may be about 2.5 millimeters. In one or more embodiments, the width of the compression element between the first end and the second end of the compression element is about 0.9 to 1.88 millimeters.

The at least one compression element may operatively connect to the second anchor 106 at any suitable location. In at least one embodiment, the compression element is operatively connected to an interior of the sliding element 202 (e.g., via one or more openings therein), which may be operatively connected to the second anchor 106, so that by connecting the compression element to the sliding element 202, the same compression may be applied by the compression element relative to connecting the compression element directly to the second anchor 106. In some embodiments, the compression element may operatively connect to an exterior or face of the sliding element 202 or any suitable portion or location of the second anchor 106.

FIG. 2B shows a perspective view of an exemplary resorbable element 108. In various embodiments, the resorbable element 108 may be a hollow cylinder having a first end 122 and a second end 124, and define circular openings 204A,B at both the first end 122 and the second end 124. In one or more embodiments, the circular openings 204A,B may include an outside diameter approximately equal to the outside diameter of the threaded portion 120 and the second end 114 (FIG. 2A). In one or more embodiments, the resorbable element 108 may encircle the sliding element 202 such that the second end 124 of the resorbable element 108 abuts the threaded portion 120 of the second anchor 106 (FIG. 2). Stated differently, in some embodiments, the sliding element 202 may pass through the openings 204A,B in the first end 122 and second end 124 of the resorbable element 108. In at least one embodiment, the first end 122 of the resorbable element 108 may abut the second end 114 of the first anchor 104.

In various embodiment, the resorbable element 108 may include one or more resorbable materials, such as, for example, PDLG (e.g., copolymer of DL-lactide and Glycolide with a 50/50 molar ratio), PLG (e.g., copolymer of L-lactide and Glycolide with a 10/90 molar ratio of L-lactide to Glycolide), poly alpha hydroxy esters (e.g., including, but not limited to, polycaprolactone, PLLA, POLA, PGA, PGLA, and/or a mixture of any of the previous), poly beta amino esters, poly anhydrides, poly dioxanone (PDO), biodegradable iron (Fe), and/or biodegradable magnesium (Mg). In one or more embodiments, after the device is implanted in a patient, the resorbable element 108 may withstand the compressive or contraction forces excited on it by the first anchor 104 and second anchor 106 so that the sliding element 202 of the second anchor 106 is prevented from translating toward and into (e.g., or further into) the second end 114 of the first anchor 104. In many embodiments, once the resorbable element 108 is substantially or completely resorbed by the body, the sliding element 202 of the second anchor 106 may be translated partially or completely into the opening of the second end 114 of the first anchor 104 such that the threaded portion 120 of the second anchor 106 abuts or nearly abuts the second end 114 of the first anchor 104.

FIG. 3 shows a side view of an exemplary delayed compression device 102 inserted into bone fragments 301, 303.

Figures 4A, 4B, 4C, 4D:
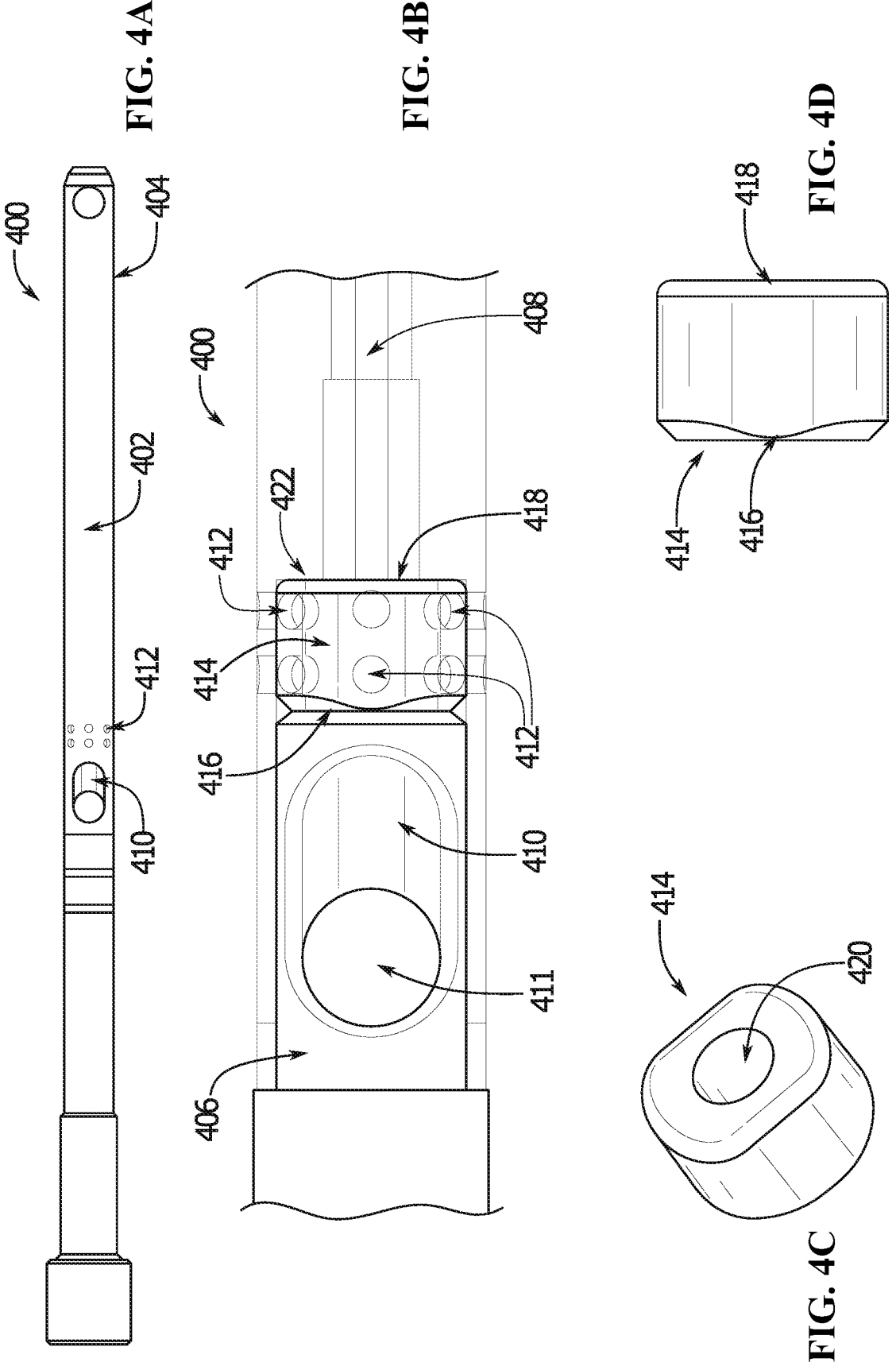
FIG. 4A is a side view of an exemplary delayed compression device, according to one embodiment of the present disclosure.
FIG. 4B shows a partial side view of an exemplary delayed compression device, according to one embodiment of the present disclosure.
FIG. 4C shows a perspective view of an exemplary resorbable element, according to one embodiment of the present disclosure.
FIG. 4D shows a side view of an exemplary resorbable element, according to one embodiment of the present disclosure.

FIG. 4A shows a side view of an alternative delayed compression device 400, according to one embodiment of the present disclosure. Further, FIG. 4B shows a partial side view of the delayed compression device 400.

In various embodiments, the delayed compression device 400 may be a bone fixation rod, nail, screw, staple, or other similar devices used to fixate bones. In at least one embodiment, the delayed compression device 400 may be an intramedullary nail or similar medical device as generally described in the following patents owned by the Applicant: U.S. Pat. No. 8,491,583 ("INTRAMEDULLARY MEDICAL DEVICE AND METHODS OF USE AND MANUFACTURE"), U.S. Pat. No. 8,118,952 ("OSTEOSYNTHETIC IMPLANTS AND METHODS OF USE AND MANUFACTURE"), and U.S. Pat. No. 7,985,222 ("OSTEOSYNTHETIC IMPLANTS AND METHODS OF USE AND MANUFACTURE"), each of which is incorporated herein by reference in its entirety.

In one or more embodiments, as shown in FIG. 4A, the delayed compression device 400 may include a rigid element 402, a proximal anchor element 404, a distal anchor element 406, and a compression element 408. In at least one embodiment, the compression element 408 is configured to translate between a between a deformed position and a non-deformed position. In various embodiments, the compression element 408 includes a rust length in the deformed position and a second length in the non-deformed position, and the first length exceeds the second length. In other words, in various embodiments, the compression element extends between a first end for attachment to a first anchor and a second end for attachment to a second anchor. In such embodiments, a distance between the first end and the second end in the deformed position is greater than a distance between the first end and the second end in the non-deformed position.

In many embodiments, as shown in FIG. 4B, the delayed compression device 400 may also include one or more resorbable elements 414. In various embodiments, the resorbable element 414 is configured to maintain the compression element 408 in the deformed state such that the compression element 408 may only move to the non-deformed state upon partial or full resorption of the resorbable element 414. In at least one embodiment, the proximal anchor element 404 may be integrally formed with the rigid element 402. In particular embodiments, the distal anchor element 406 is slidably coupled to the rigid element 402 (e.g., and thereby to the proximal anchor element 404). In some embodiments, the distal anchor element 406 is operatively coupled to the proximal anchor element 404 via the compression element 408.

In various embodiments, the rigid element 402 may slidably connect the proximal anchor element 404 and the distal anchor element 406. In the embodiment shown, the rigid element 402 is a tube-like structure that provides resistance to both torsional and bending stresses. In one or more embodiments, the rigid element 402 may be a sleeve of arbitrary cross section (e.g., a square cross section, etc.), and may have a cross section that includes ridges, channels, solid regions and/or voids. In at least one embodiment, the rigid element 402 may enclose the distal anchor element 406, limiting movement of the distal anchor element 406 to axial movement with respect to the rigid element 402. For example, in at least one embodiment, the rigid element 402 and the distal anchor element 406 may be mated and/or slidably coupled, as described further below, such that the distal anchor element 406 may move axially with respect to the rigid element 402, but may not move torsionally and/or bend (e.g., deform out of axis) with respect to the rigid element 402.

In various embodiments, the proximal anchor element 404 is connected to the rigid element 402. In one or more embodiments, the proximal anchor element 404 may be attached to the rigid element 402, or the proximal anchor element 404 may be formed with the rigid element 402 as a single piece of material. In at least one embodiment, the proximal anchor element 404 and the rigid element 402 may be portions of a single element. In another embodiment, the proximal anchor element 404 may be separated from the rigid element 402 or connected with the rigid element 402 through a flexible interconnect. In some embodiments, the end of the proximal anchor element 404 may be shaped (e.g., pointed) in order to ease insertion into a bone cavity.

In one or more embodiments, the compression element 408 may link the distal anchor element 406 and the proximal anchor element 404. In some embodiments, the compression element 408 may be strained (e.g. stretched toward an open end of the rigid element 402) via sliding the distal anchor element 406. In at least one embodiment, the distal anchor element 406 may slide relative to the proximal anchor element 404 and the rigid element 402. In at least one embodiment, the compression element 408 and the distal anchor element 406 are elements that may be connected. In another embodiment, the compression element 408 and the distal anchor element 406 are both manufactured from a single piece of material.

In various embodiments, the rigid element 402 defines slot 410, which allow the anchor holes 411 of the distal anchor element 406 to be accessed while the distal anchor element 406 is slid relative to the rigid element 402. For example, in at least one embodiment, the slot 410 may allow a bone anchor (e.g., bone screw, bone pin, rod) (not shown) to pass through the rigid element 402 without causing interactions between the bone anchor and the rigid element 402 that would axially limit the sliding of the distal anchor element 406 relative to the rigid element 402. In one or more embodiments, the slot 410 may be designed to guide axial travel of the bone anchor while coupled with the distal anchor element 406. In the embodiment shown, the slot 410 is shown large enough for the distal anchor element 406 to slide axially. For example, in some embodiments, the slot 410 may guide the bone interface device to travel axially, while limiting torsional movement of the bone interface device.

In various embodiments, the proximal anchor element 404 and distal anchor element 406 may comprise a material selected for interfacing with a bone anchor. In one or more embodiments, the material of the proximal anchor element 404 may be different than the material of the rigid element 402. In at least one embodiment, the material of the distal anchor element 406 may be different from the material of the compression element 408. In some embodiments, each material may be selected for different properties (e.g., properties adapted for holding a screw rather than properties for contracting and/or properties for compliance along an axis). In at least one embodiment, the material of the compression element 408 may include nitinol.

In one or more embodiments, the compression element 408 is substantially the same as the compression element as described above in relation to FIGS. 1, 2, and 3, or may be any suitable size needed for delaying compression between two or more bones (e.g., a size suitable for surgical needs). In one or more embodiments, the compression element 408 may include one or more compression materials that has a quality of compressing after being deformed past an elongation point, fu at least one embodiment, the one or more compression materials may include nitinol. In some embodiments, the compression element 408 may have screw threads on both ends, and the proximal anchor element 404 and the distal anchor element 406 may include screw threads that interface with the screw threads of the compression element 408, such that one end of the compression element 408 connects with the proximal anchor element 404 and the other end of the compression element 408 connects with the distal anchor element 406.

Exemplary screw threads and screw thread aspects in line with those discussed above are shown in the incorporated references, such as U.S. application Ser. No. 17/184,104.

In many embodiments, the distal anchor element 406 may fit within the rigid element 402, fu one or more embodiments, the rigid element 402 may define a cavity which encloses the distal anchor element 406 and the resorbable element 414 (as shown in FIG. 4). In one or more embodiments, the rigid element 402 may substantially encircle the resorbable element 414 and the distal anchor element 406. In at least one embodiment, the rigid element 402 may define one or more fluid holes 412 that enable bodily fluid to enter the rigid element 402 and degrade/resorb the resorbable element 414. In some embodiments, the one or more fluid holes 412 may be defined by the rigid element 402 proximate to the resorbable element 414 so that the bodily fluid may more easily degrade/resorb the resorbable element 414 (e.g., the one or more fluid holes 412 are relatively close to the resorbable element 414 so that the bodily fluid flows a short distance to interact with the resorbable element 414). In at least one embodiment, the one or more fluid holes 412 may be positioned or defined in intervals in a general circular pattern around the rigid element 402, fu many embodiments, each of the one or more fluid holes 412 may be any suitable shape (e.g., circle, quadrilateral, etc.) that allows fluid to enter into the interior of the rigid element 402. In at least one embodiment, each of the one or more fluid holes 412 are circular-shaped.

In various embodiments, as shown in FIG. 4D, the resorbable element 414 may be substantially cylindrical, having a distal end 416 and a proximal end 418. In one or more embodiments, as shown in FIG. 4C, the resorbable element 414 may define openings 420 (e.g., at both the distal end 416 and the proximal end 418 shown in FIG. 4D). The openings 420 may be circular or include any other suitable shape or combination of shapes. The openings 420 which may include an outside diameter such that the compression element 408 may pass through the openings 420 (e.g., through the resorbable element 414), and connect to the distal anchor element 406. In one or more embodiments, the distal end 416 of the resorbable element 414 abuts the distal anchor element 406, and the proximal end 418 of the resorbable element 414 abuts a cavity wall 422. In at least one embodiment, the resorbable element 414 may include one or more resorbable materials, such as, for example, PDLG (e.g., copolymer of DL-lactide and Glycolide with a 50/50 molar ratio), PLO (e.g., copolymer of L-lactide and Glycolide with a 10/90 molar ratio of L-lactide to Glycolide), poly alpha hydroxy esters (e.g., including, but not limited to, polycaprolactone, PLLA, PDLA, PGA. POLA, and/or a mixture of any of the previous), poly beta amino esters, poly anhydrides, poly dioxanone (PDO), biodegradable iron (Fe), and/or biodegradable magnesium (Mg).

In one or more embodiments, with the resorbable element 414 in the cavity, the compression element 408 may not compress and pull the distal anchor element 406 towards the proximal anchor element 404 (e.g., the distal anchor element 406 is held in place by the resorbable element 414). In many embodiments, once the resorbable element 414 is resorbed/degraded, the force caused by the compression element 408 compressing may cause the distal anchor element 406 to translate towards the proximal anchor element 404.

As will be understood from discussions herein, in at least one embodiment, the proximal anchor element 404 connects or is fixed to a first bony fragment and the distal anchor element 406 is connected to a second bony fragment (e.g., the first and second bony fragments are separate portions of the same bone that has been fractured). In various embodiments, the compression element 408 is strained when the distal anchor element 406 is pulled away from the proximal anchor element 404 (e.g., via the slot 410) and connected or fixed to the second bony fragment. Continuing with this embodiment, the compression element 408 attempts to return to its unstrained state, pulling the distal anchor element 406 towards the proximal anchor element 404, thereby compressing the first and second bony fragments. As will be further understood from discussions herein, the resorbable element 414 holds the distal anchor element 406 in place until it is resorbed, thereby delaying movement of the distal anchor element 406 towards the proximal anchor element 404 and delaying compression between the first and second bony fragments.

Figure 5:
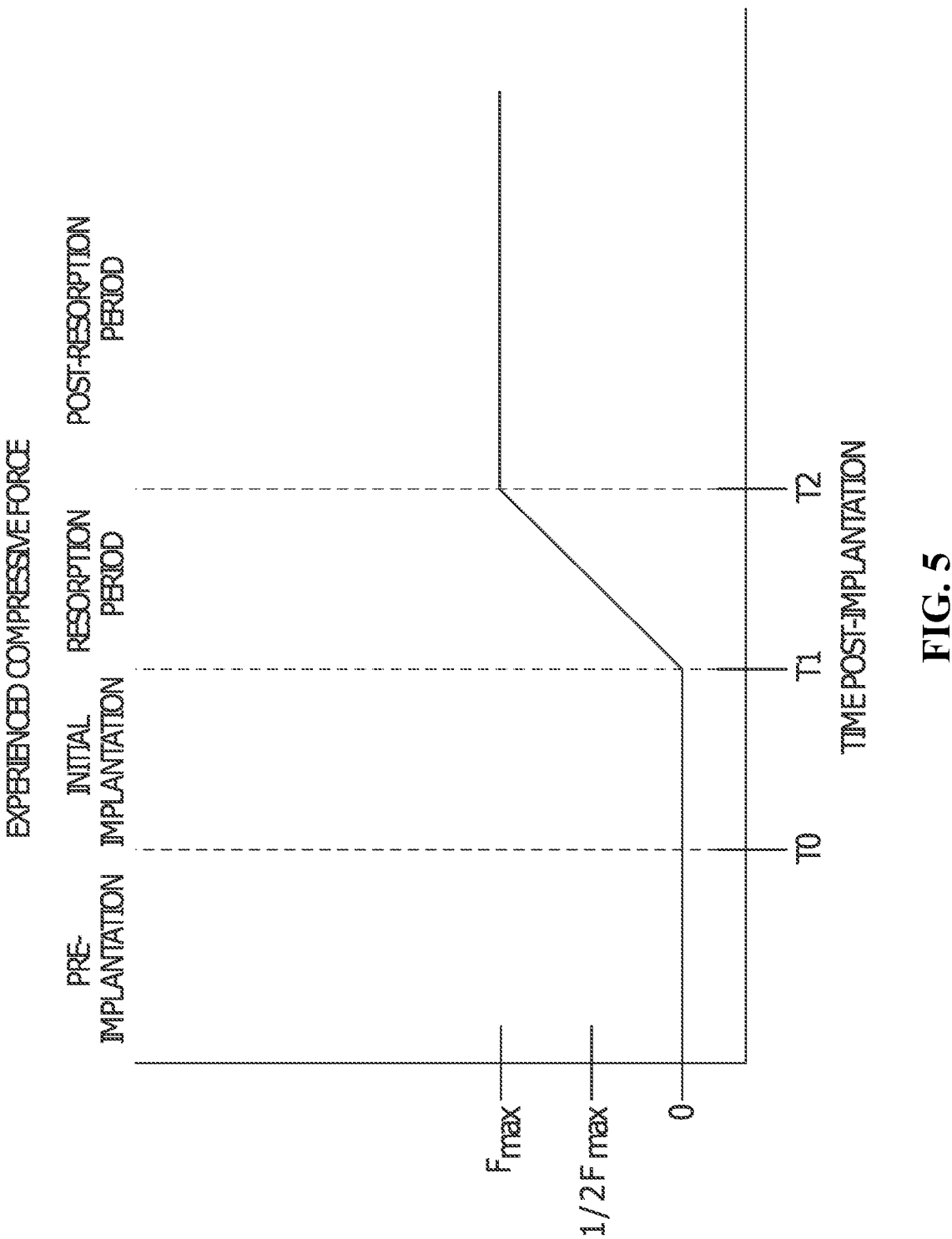
FIG. 5 is a chart of exemplary compression performance throughout implantation according to one embodiment of the present disclosure.

Now referring to FIG. 5, a chart of an exemplary compression response for an exemplary delayed compression device 102 is shown according to one embodiment. In various embodiments, the chart of FIG. 5 represents a delayed compression device tuned so that the compression forces experienced by the first and second bone fragments gradually increases.

In one or more embodiments, the chart of FIG. 5 shows the compression force experienced at the plane of contact between the first and second bone fragments over time. In many embodiments, at the initial implantation time, TO, the first and second bone fragments experience little or no compressive force from the delayed compression device 102, because the body has not yet begun to resorb the at least one resorbable element 108. In one or more embodiments, from the initial implantation time, TO, to the initial resorption period time, Tl, the first and second bone fragments experience minimal compressive force because the resorption of the at least one resorbable element 108 is insignificant such that the at least one resorbable element 108 still bears maximum compressive load. In some embodiments, starting at the initial resorption period time, TI, the at least one resorbable element 108 is being actively resorbed to the point at which the compressive load begins to shift to the first and second bone fragments, fu various embodiments, during the resorption period, the at least one resorbable element 108 is actively resorbed such that the compressive force on the first and second bone fragments increases substantially proportionally to the decrease in compressive force on the at least resorbable element 108. In at least one embodiment, at time T2, the at least one resorbable element 108 has been totally resorbed (e.g., or breaks or deteriorates to the point it is no longer effective in opposing forces from the compression element), and the first and second bone fragments bear the full compressive force of the compression element. In one or more embodiments, modifications to the surface, shape, etc. of the at least one resorbable element 108 that increase the surface area of the at least one resorbable element 108 may increase the resorption rate, thus increasing the slope of the compressive force. In a further embodiment, a delayed compression device that includes a plurality of resorbable elements may have a further delayed or modified compression response.

Figure 6:
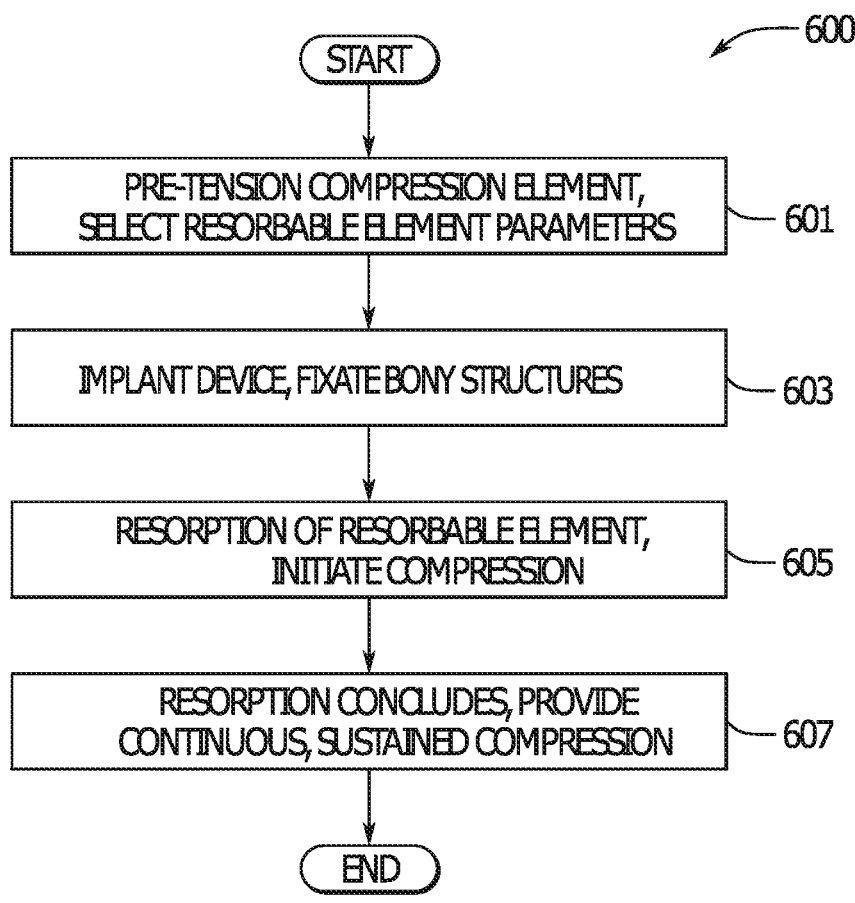
FIG. 6 is a flowchart of an exemplary fracture repair process according to one embodiment of the present disclosure.

As will be understood by one having ordinary skill in the art, the steps and processes shown in FIG. 6 (and those of all other flowcharts and sequence diagrams shown and described herein) may operate concurrently and continuously, are generally asynchronous and independent, and are not necessarily performed in the order shown.

As described in FIG. 6, an exemplary process 600 for fixation and compression of a delayed compression device is described, according to one embodiment of the present disclosure.

According to one embodiment, at step 601, the compression element and the resorbable element parameters are selected. In various embodiments, the compression element may thereafter be deformed or stretched until the compression element has the desired compression qualities for the delayed compression device. In one or more embodiments, once the compression element is deformed and the at least one resorbable element is selected based on the desired parameters, the delayed compression device is assembled.

In various embodiments, at step 603, the delayed compression device is implanted inside a patient's body and fixated to two or more bone fragments. For example, the delayed compression device is fixated to a first femur fragment and a second femur fragment. In another example, the delayed compression device is fixated to a first mandible fragment and a second mandible fragment. In another example, the delayed compression device is fixated to a calcaneus bone and a talus bone.

In one or more embodiments, at step 605, the at least one resorbable element is resorbed by the body. In one or more embodiments, as the at least one resorbable element is resorbed into the body, the compressive force of the compression element is transferred to the first and second bone fragments.

In various embodiments, at step 607, the at least one resorbable element is completely or substantially resorbed, such that the compressive force of the compression element is transferred completely to the first and second bone fragments.

In one or more embodiments, the delayed compression device may also include a kit for installing the device inside a patient. In some embodiments, the kit may include an exemplary delayed compression device, a screw driver, and a connection bolt, and instructions for preparing and installing the exemplary delayed compression device in a patient. In many embodiments, the screw driver may have a hollow interior such that the connection bolt can pass through the screw driver, and includes a plurality of pins that operatively connects with the second anchor. In one or more embodiments, the connection bolt connects the screwdriver to the delayed compression device by passing through the screw driver and connecting with the second anchor. In at least one embodiment, as the connection bolt connects with the second anchor, the plurality of pins enter openings in the second anchor, which, when the screwdriver is turned, provides the transfer of torque from the screwdriver to the delayed compression device.

Additional Embodiments

In various embodiments, the delayed compression device may include at least two anchors (a first anchor and a second anchor), at least one resorbable element, and at least one compression element. According to one embodiment, the at least one resorbable element may have a hollow body, a first end and a second end, and may define an opening at each of the first end and the second end. In many embodiments, the compression element may have a first end and a second end. In at least one embodiment, the first end of the compression element may be operatively connected to the first anchor of the anchors, and the second end of the compression element may be operatively connected to the second anchor of the anchors. In various embodiments, the hollow body of the at least one resorbable element may surround the compression element, and the first end of the at least one resorbable element abuts to the first anchor and the second end of the at least one resorbable element abuts to the second anchor, such that the compression element is substantially enclosed. In one or more embodiments, by the first and second ends of the resorbable element abutting the first and second anchors, respectively, the at least one resorbable element delays compression by functioning as a physical barrier, preventing the transfer of the compressive force (e.g., applied by the compression element) from the at least one resorbable element onto the anchors.

In one or more embodiments, as the at least one resorbable element is resorbed into the body, the compressive force from the compression element is transferred from the at least one resorbable element to the anchors, causing the anchors, and thus the attached bone fragments, to move towards the opposing anchor/bone fragment. In at least one embodiment, the at least one resorbable element includes a sleeve-like shape of a predetermined thickness sufficient to resist the compressive load of the compression element. In many embodiments, the predetermined thickness of the sleeve may be constant throughout the sleeve or may vary.

In another embodiment, the delayed compression device may include at least two anchors (a first anchor and a second anchor), at least one compression element deformed into the shape of a spring, and at least one resorbable element. In many embodiments, the compression element may have a first end and a second end. In at least one embodiment, the first end of the compression element may be operatively connected to the first anchor of the anchors, and the second end of the compression element may be operatively connected to the second anchor of the anchors. Continuing with this embodiment, the at least one resorbable element may be formed so that the at least one resorbable element is in between each ring of the at least one spring-shaped compression element, such that the at least one spring-shaped compression element is in a stretched position. Still with the same embodiment, as the body resorbs the at least one resorbable element, the rings of the at least one spring-shaped compression element may compress, thus compressing the two bone fragments, via the anchors, together. In a further embodiment, the at least one resorbable element may be modified such that one or more sections of the at least one resorbable element have different rates of resorption.

In yet another embodiment, the delayed compression device may include at least two resorbable elements (a first resorbable element and a second resorbable element) such that the delayed compression device compresses in two stages. In this embodiment, the delayed compression device may also include at least two anchors (a first anchor and a second anchor), at least one compression device having a first end operatively connected to the first anchor of the anchors and a second end operatively connected the second anchor of the anchors, a first sliding element and a second sliding element, and a middle body. In one or more embodiments, the first sliding element is operatively connected to the first anchor of the anchors and the second sliding element is operatively connected to the second of the anchors. In one or more embodiments, the middle body may include a hollow body, a first end defining a first opening, and a second end defining a second opening. In at least one embodiment, the first end of the middle body abuts the first resorbable element, and the second end of the middle body abuts the second resorbable element. In this embodiment, the at least two resorbable elements prevent the compression element from compressing by acting as physical barriers so that the first sliding element and the second sliding element cannot initially move. Continuing with this embodiment, as the at least two resorbable elements are resorbed, the compressive force from the compression element is transferred from the at least two resorbable elements to the anchors, causing the first sliding element and the second sliding element to be compressed towards the middle body. In many embodiments, the at least two resorbable elements may be the same shape and size such that the resorption rate of each of the at least two resorbable elements is equivalent, or may be different shapes and sizes and have different features such that the resorption rates of each of the at least two resorbable elements is different.

In an alternate embodiment, the middle body may cover or otherwise protect one of the at least two resorbable elements from being resorbed upon implanting the device in a patient. Continuing in this embodiment, once the uncovered resorbable element is resorbed, the middle body may slide, via the first sliding element or otherwise cause the covered resorbable element to become uncovered or unprotected, such that the newly uncovered resorbable element may now be resorbed. In this embodiment, once the second resorbable element is resorbed, the device may further compress via the second sliding element.

In yet another embodiment, the delayed compression device may be used to provide compression onto a first body part, a second body part, and a third body part. For example, in at least one embodiment, the delayed compression device may be used to compress three bone fragments together, by utilizing one of the three bone fragments as a middle anchor point and pulling the other two bone fragments towards the middle fragment. Continuing with this example, the delayed compression device may be bored through the middle bone fragment and anchored securely thereto, so that part of the delayed compression device protrudes from one side of the middle bone fragment, and the other part of the delayed compression device protrudes from the opposing side of the middle bone fragment. Still continuing with this example, each opposing part of the delayed compression device may be operatively connected via an anchor to each of the second and third bone fragments, so that the first bone fragment is operatively connected with the third bone fragment via the delayed compression device bored through (and anchored to) the middle bone fragment.

In this embodiment, the delayed compression device may include at least three anchors (a first anchor, a second anchor, and a third anchor), at least two resorbable elements (a first resorbable element and a second resorbable element), at least one compression element, and at least two sliding elements. Continuing in this embodiment, each opposing part of the delayed compression device may have one resorbable element, one anchor, and one sliding element. In this embodiment, the compression device may be operatively connected to the anchor in the first bone fragment and to the anchor in the third bone fragment.

In another embodiment, the compression element may be two compression elements (e.g., a first compression element and a second compression element), such that a first compression element is operatively connected to the first anchor and the middle anchor, and a second compression element is operatively connected to the third anchor and the middle anchor. Continuing in this embodiment, the second anchor, attached to the middle bone fragment, may have two attachment points on opposing sides of the second body part. In one or more embodiments, the first compression element has a first end and a second end, and the second compression element has a first end and a second end. In at least one embodiment, the first end of the first compression element may be operatively connected to the first anchor, the second end of the first compression element may be operatively connected to the second anchor, the first end of the second compression element may be operatively connected to the second anchor, and the second end of the second compression element may be operatively connected to the third anchor. Still continuing with this embodiment, the first resorbable element may encircle the first compression element, and the other one of the at least two resorbable elements may encircle the second compression element. According to this embodiment, as the at least two resorbable elements are resorbed into the body, the compressive forces from the at least two compression elements are transferred from the at least two resorbable elements to the at least three anchors, causing the at least two sliding elements to compress. In a further embodiment, each of the at least two resorbable elements may be different shapes, sizes, or have different features such that the resorption rates for each separate at least two resorbable elements is different.

In another embodiment, the delayed compression device may include a rotational element such that one or more anchors rotate as the delayed compression device is compressed. In this embodiment, the rotation may be realized by adding a rotational element to the exemplary embodiment described above. In various embodiments, the rotational element may be a screw-like connection between the at least one sliding element and the first anchor. In at least one embodiment, the at least one sliding element may include screw threads, and the hollow inside of the second end of the first anchor may include screw threads that fit the screw threads of the at least one sliding element. In one or more embodiments, as the at least one resorbable element is resorbed, the at least one sliding element is compressed towards the first anchor, and the at least one sliding element is forced to rotate via the rotational element, causing a rotational force to be put onto the first anchor and the second anchor. In further embodiments, the delayed compression device may include rotational elements of different rotational degrees.

In another embodiment, the delayed compression device may include a resorbable element that works in tension to delay compression, rather than in compression (e.g., by blocking a sliding element from translating towards a first anchor—in this embodiment the resorbable element is not in between the sliding element and the opposing anchor). In such an embodiment, the resorbable element may hold one anchor from translating towards the opposing anchor. For example, in at least one embodiment, a delayed compression device may include a first anchor, a second anchor, a sliding element, and an extension piece that connects to the second anchor or sliding element (e.g., connects on one end of the second anchor or sliding element, opposite the end that connects to the first anchor), and the resorbable element may be a part of the connection between the extension piece and the second anchor such that the resorbable element holds the second anchor in place, with some distance between the second anchor and the first anchor, (e.g., rather than blocking) and prevents the second anchor from translating towards the first anchor. In some embodiments, an example of a part that may be made of the resorbable material (e.g., would be the resorbable element) is the connection bolt shown and described in U.S. application Ser. No. 17/184, 104, which is incorporated herein by reference.

Continuing with this embodiment, once the resorbable element is resorbed, the sliding element is no longer held in place and translates (or attempts to translate) towards the first anchor.

Figure 7:
FIG. 7 is a side view of an alternative exemplary delayed compression device, according to one embodiment of the present disclosure.

As one example, FIG. 7 shows an alternative exemplary delayed compression device 700. In various embodiments, the delayed compression device 700 is configured to operate in tension to delay compression. In one or more embodiments, the delayed compression device 700 includes, but is not limited to, an outer body 701, sliding element 703, resorbable element 705, and compression element 707. In at least one embodiment, the sliding element 701 includes a first end 704 and a second end 706. In various embodiments, the sliding element 701 is attached to the resorbable element 705 at the first end 704 and attached to the compression element 707 toward the second end 706. In one or more embodiments, the compression element 707 applies a tensile force to the sliding element 703 for translating the sliding element 703 further into the outer body 701, fu at least one embodiment, the resorbable element 705 prevents the sliding element 703 from translating further into the outer body 701. In various embodiments, following at least partial resorption of the resorbable element 705, the sliding element 703 is rendered capable of translating further into the outer body 701 under tensile force from the compression element 707.

While various aspects have been described in the context of a preferred embodiment, additional aspects, features, and processes of the claimed devices and processes will be readily discernible from the description herein, by those of ordinary skill in the art. Many embodiments and adaptations of the disclosure and claimed devices and processes other than those herein described, as well as many variations, modifications, and equivalent arrangements and processes, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed devices and processes. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed devices and processes. In addition, some steps may be carried out simultaneously, contemporaneously, or in synchronization with other steps.

The embodiments were chosen and described in order to explain the principles of the claimed devices and processes and their practical application so as to enable others skilled in the art to utilize the devices and processes and various embodiments and with various modifications as are suited to the particular use contemplated. Alternative embodiments will become apparent to those skilled in the art to which the claimed devices and processes pertain without departing from their spirit and scope. Accordingly, the scope of the claimed devices and processes is defined by the appended claims rather than the foregoing description and the exemplary embodiments described therein.

What is claimed is:

1. A medical device comprising:
a compression element;
a first anchor for attachment to a first bone fragment;
a second anchor coupled to the first anchor via the compression element, the second anchor for attachment to a second bone fragment;
the compression element comprising nitinol and attached to the first anchor and the second anchor, the compression element being deformed to a deformed position; and
a resorbable element holding the compression element in the deformed position, wherein:
the resorbable element comprises a material, size, and shape such that the resorbable element resorbs in a predetermined amount of time after insertion into a patient; and
after the predetermined amount of time following insertion into the patient, the resorbable element is resorbed and the compression element moves from the deformed position to a non-deformed position compressing the first bone fragment and the second bone fragment,
wherein the shape of the resorbable element is a substantially cylindrical shape.

2. The medical device of claim 1, wherein the predetermined amount of time comprises about 2-8 weeks.

3. The medical device of claim 2, wherein the first anchor comprises screw threads.

4. The medical device of claim 3, wherein the resorbable element comprises one or more of the following materials:
DL-lactide and Glycolide with a 50/50 molar ratio;
L-lactide and Glycolide with a 10/90 molar ratio of L-lactide to Glycolide;
poly alpha hydroxy esters;
poly beta amino esters;
poly anhydrides, poly dioxanone (PDO);
biodegradable iron (Fe); and/or
biodegradable magnesium (Mg).

5. A medical device comprising:

a compression element;

a first anchor for attachment to a first bone fragment;

a second anchor coupled to the first anchor via the compression element, the second anchor for attachment to a second bone fragment;

the compression element being between the first anchor and the second anchor; and a resorbable element maintaining the first anchor and the second anchor at a first distance, wherein:

the resorbable element is configured to at least partially resorb after insertion into a patient; and after the resorbable element is at least partially resorbed, the compression element forces the first anchor and/or the second anchor to translate such that the first anchor and the second anchor are at a second distance, thereby compressing the first bone fragment and the second bone fragment, wherein the shape of the resorbable element is a substantially cylindrical shape.

6. The medical device of claim 5, wherein the resorbable element comprises one or more materials from the group comprising: DL-lactide and Glycolide with a 50/50 molar ratio, L lactide and Glycolide with a 10/90 molar ratio of L-lactide to Glycolide, poly alpha hydroxy esters, poly beta amino esters, poly anhydrides, poly dioxanone (PDO), biodegradable iron (Fe), and biodegradable magnesium (Mg).

7. The medical device of claim 5, wherein:

the medical device comprises a midpoint between the First anchor and the second anchor; and after the resorbable element is at least partially resorbed, the compression element forces the first anchor and/or the second anchor to translate toward the midpoint.

8. The medical device of claim 7, wherein the resorbable element is between the first anchor and the second anchor.

9. The medical device of claim 5, wherein the compression element passes through the resorbable element.

10. The medical device of claim 5, wherein the medical device is a screw.

11. The medical device of claim 5, wherein the medical device is an intramedullary nail.

12. A method comprising:

coupling a first anchor of a medical device to a first bone fragment within a patient;

coupling a second anchor of the medical device to a second bone fragment within the patient; and positioning the first bone fragment adjacent to the second bone fragment in a first position, wherein the positioning comprises the steps of:

coupling the first anchor to the second anchor by a compression element;

holding the first anchor and the second anchor in a fixed position via a resorbable element comprising a substantially cylindrical shape; and upon at least partial resorption of the resorbable element, the first anchor and/or the second anchor translate toward a midpoint of the medical device via the compression element, thereby moving the first bone fragment and the second bone fragment to a second position and compressing the first bone fragment and the second bone fragment.

13. The method of claim 12, wherein in the first position, the first bone fragment and the second bone fragment are uncompressed.

14. The method of claim 13, wherein in the first position, the first bone fragment and/or the second bone fragment experience micro-motion.

15. The method of claim 14, wherein the resorbable element comprises one or more materials from the group comprising: DL-lactide and Glycolide with a 50/50 molar ratio, L-lactide and Glycolide with a 10/90 molar ratio of L-lactide to Glycolide, poly alpha hydroxy esters, poly beta amino esters, poly anhydrides, poly dioxanone (PDO), biodegradable iron (Fe), and biodegradable magnesium (Mg).

16. The method of claim 15, wherein the resorbable element is between the first anchor and the second anchor.

17. The method of claim 16, wherein the compression element comprises nitinol.

* * * * *